United States Patent [19]

Mair

[11] 4,424,701
[45] Jan. 10, 1984

[54] ULTRASONIC MEASURING SENSOR FOR THE FIXING STATION OF A NON-MECHANICAL PRINTING OR COPYING DEVICE

[75] Inventor: Eduard Mair, Munich, Fed. Rep. of Germany

[73] Assignee: Siemens Aktiengesellschaft, Berlin & Munich, Fed. Rep. of Germany

[21] Appl. No.: 360,432

[22] Filed: Mar. 22, 1982

[30] Foreign Application Priority Data

Mar. 26, 1981 [DE] Fed. Rep. of Germany ....... 3112003

[51] Int. Cl.³ ............................................. G01N 29/02
[52] U.S. Cl. ........................................ 73/24; 118/712; 73/290 V
[58] Field of Search ............... 73/24, 30, 32 A, 290 V; 355/3 FU; 118/712, 713; 430/30

[56] References Cited

U.S. PATENT DOCUMENTS 3,049,810  8/1962  Iwerks .................................. 34/151
3,697,936  10/1972  Zacharias, Jr. et al. ............. 340/3 E
4,313,343  2/1982  Kobayashi et al. ................. 73/290 V Primary Examiner—Stephen A. Kreitman
Assistant Examiner—John E. Chapman, Jr.
Attorney, Agent, or Firm—Hill, Van Santen, Steadman & Simpson

[57] ABSTRACT

An ultrasonic measuring sensor for the fixing station of a non-mechanical printing or copying device has an electroacoustical transducer for both transmitting and receiving ultrasonic oscillation, and a reflector spaced a distance from the transducer for reflecting the oscillation transmitted by the transducer back to the transducer. The measuring path between the transducer and the reflector is surrounded by a fine mesh net having a mesh size which is significantly smaller than the wavelength of the ultrasonic oscillation. The mesh of the net is selected so as to permit the vapor concentration inside of the net to follow the changes in the average concentration at the fixing station with sufficient rapidity while shielding the measuring path against brief and topically limited concentration fluctuations.

3 Claims, 1 Drawing Figure

U.S. Patent   Jan. 10, 1984   4,424,701
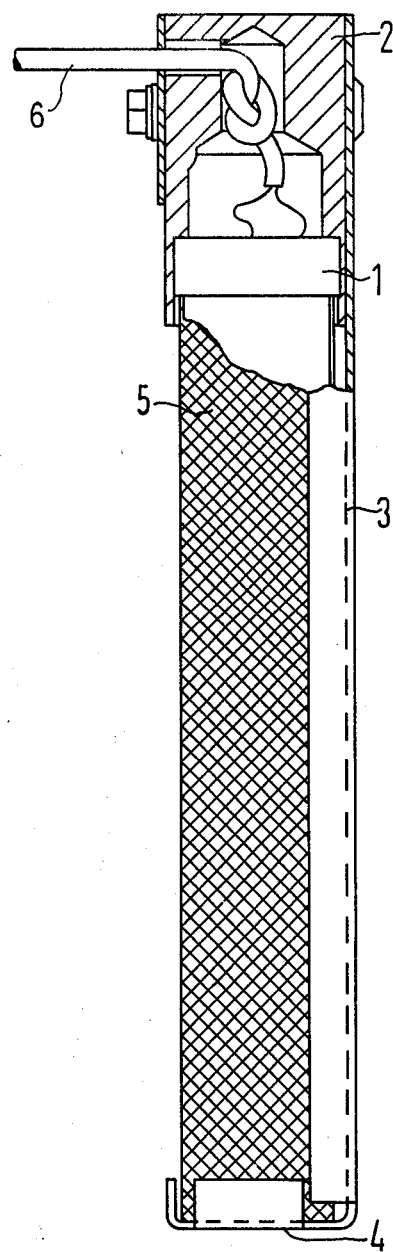

ULTRASONIC MEASURING SENSOR FOR THE FIXING STATION OF A NON-MECHANICAL PRINTING OR COPYING DEVICE

BACKGROUND OF THE INVENTION

1. Field of the Invention

The present invention relates to ultrasonic measuring devices and in particular to an ultrasonic measuring device for use in monitoring the concentration of solvent vapor in the fixing station of a copying machine.

2. Description of the Prior Art

It is known from U.S. Pat. No. 3,049,810 to fix the toner images applied to a moving paper web in a fixing station of a printing or copying device by the use of solvent vapor. The vapor consisting of freon and methylene chloride dissolves the toner so that it can penetrate into the paper. The fixing station in which this process takes place may consist, for example, of a container or housing including an evaporation location by means of which the solvent is converted from a liquid into a vapor. The paper web is conducted through the housing and is exposed to the solvent vapor inside the housing. A condensation trap is commonly attached in front of the container opening for preventing the escape of solvent vapor into the environment.

A problem relating to the above known process and apparatus is that a perfect fixing of the toner images on the paper web can be achieved only when the solvent vapor has a specific concentration. It is therefore necessary that the concentration of the solvent vapor be determined within the fixing station by means of a measuring device.

Ultrasonic measuring devices operating on the principle that the transit time of an ultrasonic signal in a medium such as air varies depending upon the concentration of a vapor in the air are also known to those skilled in the art. One such ultrasonic measuring device is known, for example, from German AS No. 2,024,882 in which the electroacoustical transducer serves the function of transmitting the ultrasonic oscillation as well as receiving the oscillation which has been reflected by a reflector.

Ideally a device disposed in the fixing station of a printing or copying machine for providing an electronic signal corresponding to the concentration of the solvent vapor therein should provide a signal to an evaluation logic means connected to the sensor for determining whether the vapor concentration is within the specified range for proper operation, whether new solvent must be supplied and evaporated, or whether deviations from the specified value are so large that the printing or copying machine must be shut off.

A problem which is associated with any vapor concentration monitoring means which is used to control the operation of a device is that temporary disruptions in the vapor concentration may occur within the volume of air monitored by the sensor which may result in a changing of the density of the fixing agent vapor which are temporally and topically limited and therefore are not representative of the average density of the solvent vapor in the entire volume of the fixing station. Such disruptions may be caused by, for example, the formation of eddies due to spontaneous evaporation when the solvent is injected into the fixing station, thermal stratifications between the heated evaporation location and the condensation trap, and turbulences due to the moving paper web. These usually brief and spatially limited disruptions of the homogeneous distribution of the solvent vapor mixture have only a negligible influence on the fixing quality. The minimally different effect of the solvent in the vicinity of such temporary disruptions is balanced out over the longer fixing path.

Such disruptions do, however, significantly vitiate the measurements of the vapor concentration and the evaluation thereof in the limited volume of conventional detection devices. Diffractions of the ultrasonic wave may be caused which result in interference patterns, particularly due to the topical fluctuations of the vapor concentration. Such interference patterns may partially or entirely cancel the echo from the ultrasonic reflector or prevent the generation of useable electrical pulses at the receiver due to out of phase excitation of various portions of the sound-absorbing surface of the ultrasonic transducer.

SUMMARY OF THE INVENTION

It is an object of the present invention to provide an ultrasonic measuring sensor for use in the fixing station of a non-mechanical printing or copying device which can accurately monitor the solvent concentration in the station and which is substantially immune to localized concentration disruptions.

The above object is inventively achieved in an ultrasonic measuring sensor wherein the measuring path disposed between the electroacoustical transducer and the reflector disposed opposite thereto is surrounded by a fine mesh net having a mesh size which is significantly smaller than the wavelength of the ultrasonic oscillation.

BRIEF DESCRIPTION OF THE DRAWING

The single FIGURE is a side view, partly in section, showing an ultrasonic measuring device constructed in accordance with the principles of the present invention.

DESCRIPTION OF THE PREFERRED EMBODIMENTS

A device for monitoring the concentration of solvent vapor in the fixing station of a printing or copying device constructed in accordance with the principles of the present invention is shown in the FIGURE. The device includes an ultrasonic transducer 1 which is seated in a housing 2. The housing 2 is comprised of a dimensionally stable, oscillation-damping synthetic such that any acoustical coupling between transducer 1 and the additional elements secured to the housing 2 is substantially minimized, if not eliminated. The device further includes a U-shaped bow 3 which is attached to the housing 2 at a point close to the transducer 1. The base of the U-shaped bow 3 is disposed substantially parallel to the transducer 1 and forms a reflector 4 at which the ultrasonic waves emitted by the transducer 1 are reflected and returned to the transducer 1. The distance between the transducer 1 and the reflector 4 may be, for example, 150 millimeters and defines the measuring path which is traversed twice by the ultrasonic signals. The volume between the transducer 1 and the reflector 4 is surrounded by a sieve tube 5 consisting of a fine mesh net. In a preferred embodiment, the net consists of interwoven wires having a diameter of approximately 0.06 millimeters which are interwoven such that the openings which arise have an edge length of approximately 0.025 millimeters. An open sieve surface of approximately 10% is thus obtained. This value is a compromise in order to achieve a vapor concentration on the inside of the sieve tube 5 which tracks changes in the average concentration in the overall fixing station in which the device is situated with sufficient rapidity while shielding the interior of the sieve tube 5 against brief and topically limited concentration fluctuations. Interference phenomena caused by diffractions of the acoustical field in the measuring path are eliminated to a significant extent so that the reflected signals are not falsified by such localized disruptions. The sieve tube 5 additionally substantially suppresses false echo signals which may otherwise be present from the surrounding environment.

The reflected signals from the reflector 4 are received by the transducer 1 and transmitted via a lead 6 to suitable postconnected logic evaluation circuitry of the type known to those skilled in the technology of measurement devices for evaluating the signal and generating appropriate control signals for governing the operation of the printing or copying machine.

Although modifications and changes may be suggested by those skilled in the art it is the intention of the inventor to embody within the patent warranted hereon all changes and modifications as reasonably and properly come within the scope of his contribution to the art.

I claim as my invention:

1. An ultrasonic measuring sensor for use in the fixing station of a non-mechanical printing or copying device for measuring the solvent vapor concentration therein comprising:

an electroacoustical transducer for transmitting an ultrasonic signal and for receiving said signal after reflection thereof;

a reflector disposed a distance from said ultrasonic transducer for reflecting ultrasonic signals therefrom back to said transducer, said transducer generating an electrical signal corresponding to the transmit time of said signal between said transducer and said reflector which varies according to the amount of solvent vapor present between said transducer and said reflector; and a fine mesh net enclosing the volume between said transducer and said reflector, said net having a mesh size which is significantly smaller than the wavelength of said ultrasonic signal for substantially preventing brief localized disruptions in said solvent vapor concentration from penetrating said mesh and falsifying said electronic signal.

2. The ultrasonic measuring sensor of claim 1 wherein said fine mesh net consists of a plurality of interwoven wires having a diameter of approximately 0.06 millimeters which are interwoven such that said net has an open sieve surface of approximately 10%.

3. The ultrasonic measuring sensor of claim 1 wherein said distance between said transducer and said reflector is approximately 150 millimeters.

* * * * *